United States Patent [19]

Tomita et al.

[11] Patent Number: 4,579,860
[45] Date of Patent: Apr. 1, 1986

[54] ISOXAZOLINONE DERIVATIVES, PROCESS FOR THEIR PREPARATION AND INSECTICIDAL AND ACARICIDAL COMPOSITIONS CONTAINING THEM

[75] Inventors: Kazuo Tomita; Tadashi Murakami, both of Hiromachi; Hideakira Tsuji, Shiga; Keigo Matsumoto, Shiga; Katsuhiro Fujita, Shiga, all of Japan

[73] Assignee: Sankyo Company, Limited, Tokyo, Japan

[21] Appl. No.: 491,857

[22] Filed: May 5, 1983

[30] Foreign Application Priority Data

May 10, 1982 [JP] Japan .................................. 57-77793

[51] Int. Cl.$^4$ .................... C07D 261/12; A01N 47/18
[52] U.S. Cl. ...................................... 514/380; 548/243
[58] Field of Search ................ 548/243, 213; 424/272

[56] References Cited

U.S. PATENT DOCUMENTS 4,060,402 11/1977 Tomita et al. ....................... 548/243

FOREIGN PATENT DOCUMENTS 2881 7/1979 European Pat. Off. ............ 548/245
34456 8/1981 European Pat. Off. ................ 71/88
51877 5/1982 European Pat. Off. ............ 548/243
1044636 4/1976 Japan ..................................... 424/272
1245238 9/1971 United Kingdom ................ 548/243

Primary Examiner—Donald G. Daus
Assistant Examiner—G. Hendricks
Attorney, Agent, or Firm—Frishauf, Holtz, Goodman & Woodward

[57] ABSTRACT

Compounds of formula (I):

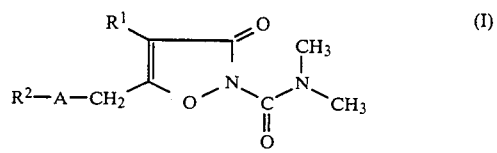

(wherein $R^1$ represents a hydrogen or halogen atom $R^2$ represents an alkyl, alkenyl, alkynyl, optionally substituted aralkyl or optionally substituted aryl group and A represents a sulphur atom or a sulphinyl or sulphonyl group) have insecticidal and acaricidal activity and, when formulated in suitable compositions for agricultural or horticultural use, can be used to protect plants from attack by insects or acarids.

16 Claims, No Drawings

ISOXAZOLINONE DERIVATIVES, PROCESS FOR THEIR PREPARATION AND INSECTICIDAL AND ACARICIDAL COMPOSITIONS CONTAINING THEM

BACKGROUND TO THE INVENTION

The present invention relates to a series of new isoxazolinone derivatives, to processes for preparing them and to insecticidal and acaricidal compositions containing these new derivatives.

Insects and acarids cause considerable damage to plants and can represent a serious danger to health; at best, they are a major nuisance. Accordingly, large sums are spent on their destruction. Although many insecticides and acaricides are available, a large number of these have to be used with care because they can endanger animals or because of their phytotoxicity. Moreover, because of their short life cycles, insects and acarids can develop immunity to many of the commonly used insecticides and acaricides and, accordingly, their is always a continuing need for new compounds exhibiting insecticidal and acaricidal properties.

A number of compounds containing the isoxazole system are known to exhibit insecticidal and/or acaricidal activity. For example, Japanese patent specification (published for opposition) No. 45367/78 discloses a class of compounds which may be represented by the formula:

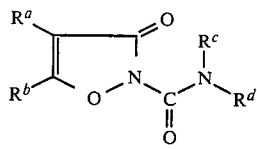

in which: $R^a$ represents a hydrogen atom, a lower alkyl group or a halogen atom; and $R^b$, $R^c$ and $R^d$ each represents a lower alkyl group. These compounds are said to be useful for insecticidal and acaricidal compositions, but they have been found to possess insufficient insecticidal activity for practical use.

There has also been proposed in copending U.S. patent application Ser. No. 318,602, filed Nov. 5, 1981, to the present assignees, a series of carbamoyloxyisoxazole derivatives, which may be represented by the formula:

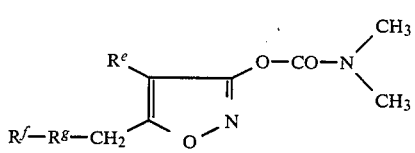

(in which: $R^e$ represents a hydrogen or halogen atom; $R^f$ represents a $C_1$-$C_6$ alkyl group; and $R^g$ represents an oxygen or sulphur atom or a sulphinyl or sulphonyl group). These compounds were demonstrated to have good insecticidal activity.

We have now discovered a series of isoxazolinone derivatives which have superior insecticidal activities, particularly systemic activity, to the known compounds and which, in addition, have good acaricidal activity. They are particularly suitable for the control of aphids and mites.

BRIEF SUMMARY OF INVENTION

It is, therefore, an object of the invention to provide a series of new isoxazolinone derivatives having good insecticidal and acaricidal activities.

It is a further object of the invention to provide an insecticidal composition wherein the active ingredient comprises at least one of said isoxazolinone derivatives.

The novel isoxazolinone derivatives of the present invention may be represented by the formula (I):

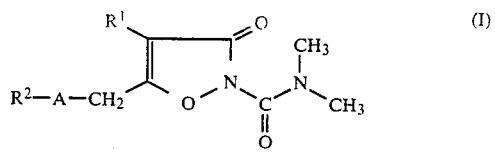

in which:
$R^1$ represents a hydrogen atom or a halogen atom;
$R^2$ represents an alkyl group, a $C_2$-$C_6$ alkenyl group, a $C_2$-$C_6$ alkynyl group, an aralkyl group, a substituted aralkyl group, an aryl group or a substituted aryl group; and
A represents a sulphur atom, a sulphinyl group or a sulphonyl group.

DESCRIPTION OF PREFERRED EMBODIMENTS

In the compounds of the invention, where $R^1$ represents a halogen atom, it may be a chlorine, bromine, iodine or fluorine atom, preferably a chlorine or bromine atom.

Where $R^2$ represents an alkyl group, it may be a straight or branched chain alkyl group, preferably having from 1 to 8 carbon atoms, for example a methyl, ethyl, propyl, isopropyl, butyl, t-butyl, pentyl or octyl group, more preferably a $C_1$-$C_4$ alkyl group. Where $R_2$ represents a $C_2$-$C_6$ alkenyl group, it is preferably an allyl or methallyl group. Where $R^2$ represents a $C_2$-$C_6$ alkynyl group, it is preferably a 1-propynyl or 2-propynyl group. Where $R^2$ represents an aralkyl group, it is preferably a benzyl or phenethyl group and may have one or more substituents (for example halogen atoms, $C_1$-$C_6$ alkyl groups or $C_1$-$C_6$ alkoxy groups) on the benzene ring; the most preferred aralkyl group is a benzyl group. Where $R^2$ represents an aryl group, it is preferably a phenyl or naphthyl group, which may have one or more substituents (for example halogen atoms, $C_1$-$C_6$ alkyl groups or $C_1$-$C_6$ alkoxy groups); it is preferably a phenyl group.

Of the compounds of formula (I), the most preferred compounds are those in which:
$R^1$ represents a hydrogen, chlorine or bromine atom;
$R^2$ represents a straight-chain $C_1$-$C_4$ alkyl group or a $C_3$-$C_4$ alkenyl group; and
A represents a sulphur atom, a sulphinyl group or a sulphonyl group.

Representative examples of compounds of the invention are listed below; the numbers appended to the compounds in the following list are used to identify those compounds hereinafter:

1. 2-dimethylcarbamoyl-5-methylthiomethyl-4-isozazolin-3-one, melting at 91°–92° C.;
2. 2-dimethylcarbamoyl-5-ethylthiomethyl-4-isoxazoline-3-one, $n_D^{24}=1.5378$;
3. 2-dimethylcarbamoyl-5-propylthiomethyl-4-isoxazolin-3-one, $n_D^{24}=1.5337$;

4. 2-dimethylcarbamoyl-5-isopropylthiomethyl-4-isoxazolin-3-one, $n_D^{25} = 1.5297$;
5. 5-butylthiomethyl-2-dimethylcarbamoyl-4-isoxazolin-3-one, $n_D^{25} = 1.5256$;
6. 5-allylthiomethyl-2-dimethylcarbamoyl-4-isoxazolin-3-one, $n_D^{25} = 1.5506$;
7. 2-dimethylcarbamoyl-5-methallylthiomethyl-4-isoxazolin-3-one, $n_D^{25} = 1.5448$;
8. 4-chloro-2-dimethylcarbamoyl-5-methylthiomethyl-4-isoxazolin-3-one, melting at 51°–52° C.;
9. 4-chloro-2-dimethylcarbamoyl-5-ethylthiomethyl-4-isoxazolin-3-one, $n_D^{22} = 1.5454$;
10. 4-chloro-2-dimethylcarbamoyl-5-propylthiomethyl-4-isoxazolin-3-one, $n_D^{23} = 1.5388$;
11. 4-chloro-2-dimethylcarbamoyl-5-isopropylthiomethyl-4-isoxazolin-3-one, melting at 55°–57° C.;
12. 5-butylthiomethyl-4-chloro-2-dimethylcarbamoyl-4-isoxazolin-3-one, $n_D^{22.5} = 1.5327$;
13. 5-t-butylthiomethyl-4-chloro-2-dimethylcarbamoyl-4-isoxazolin-3-one, $n_D^{22} = 1.5342$;
14. 5-allylthiomethyl-4-chloro-2-dimethylcarbamoyl-4-isoxazolin-3-one, $n_D^{22} = 1.5558$;
15. 4-chloro-2-dimethylcarbamoyl-5-methallylthiomethyl-4-isoxazolin-3-one, $n_D^{25} = 1.5496$;
16. 4-chloro-2-dimethylcarbamoyl-5-(2-propynyl)thiomethyl-4-isoxazolin-3-one, melting at 106°–107° C.;
17. 4-chloro-2-dimethylcarbamoyl-5-phenylthiomethyl-4-isoxazolin-3-one, melting at 77°–78° C.;
18. 5-benzylthiomethyl-4-chloro-2-dimethylcarbamoyl-4-isoxazolin-3-one, $n_D^{23} = 1.5814$;
19. 4-bromo-2-dimethylcarbamoyl-5-methylthiomethyl-4-isoxazolin-3-one, melting at 49°–50° C.;
20. 4-bromo-2-dimethylcarbamoyl-5-ethylthiomethyl-4-isoxazolin-3-one, $n_D^{23.5} = 1.5595$;
21. 2-dimethylcarbamoyl-5-methylsulphinylmethyl-4-isoxazolin-3-one, $n_D^{24} = 1.5502$;
22. 2-dimethylcarbamoyl-5-ethylsulphinylmethyl-4-isoxazolin-3-one, $n_D^{24} = 1.5336$;
23. 2-dimethylcarbamoyl-5-methylsulphonylmethyl-4-isoxazolin-3-one, melting at 142°–143° C.;
24. 2-dimethylcarbamoyl-5-ethylsulphonylmethyl-4-isoxazolin-3-one, melting at 100°–101° C.;
25. 4-chloro-2-dimethylcarbamoyl-5-methylsulphinylmethyl-4-isoxazolin-3-one, melting at 103°–104° C.
26. 4-chloro-2-dimethylcarbamoyl-5-ethylsulphinylmethyl-4-isoxazolin-3-one, melting at 79°–80° C.;
27. 4-chloro-2-dimethylcarbamoyl-5-methylsulphonylmethyl-4-isoxazolin-3-one, melting at 129°–129.5° C.;
28. 4-chloro-2-dimethylcarbamoyl-5-ethylsulphonylmethyl-4-isoxazolin-3-one, melting at 82.5°–83.5° C.

The compounds of the invention may be prepared by the processes illustrated in the following reaction scheme:

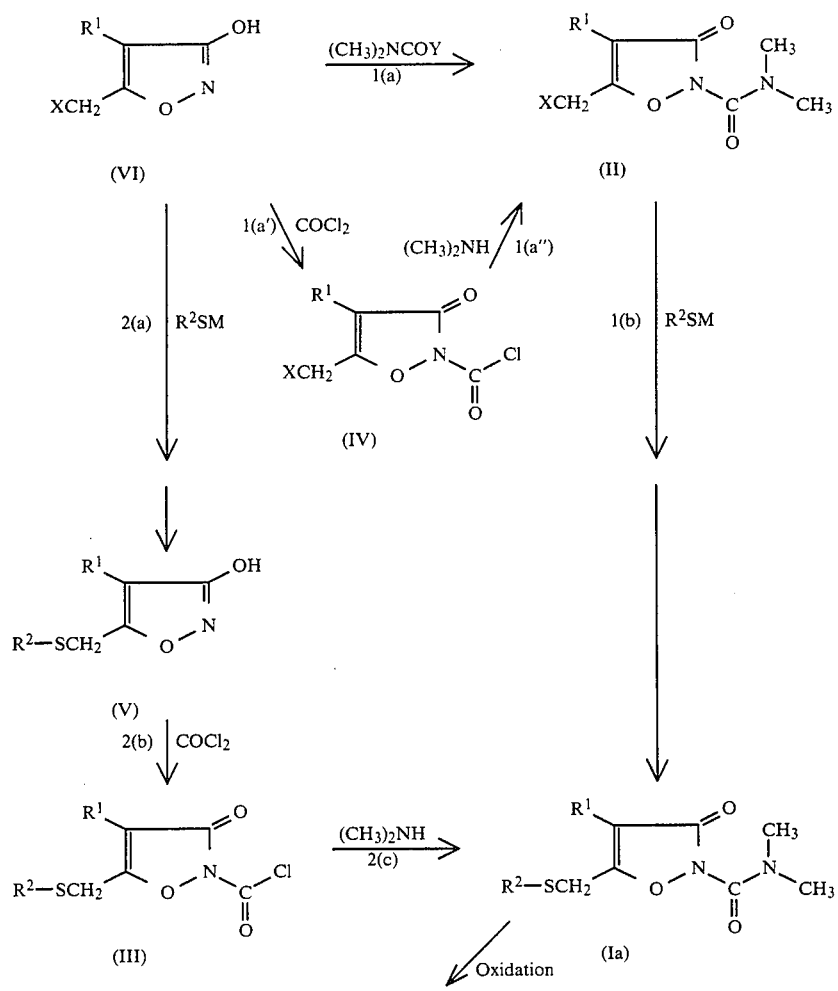

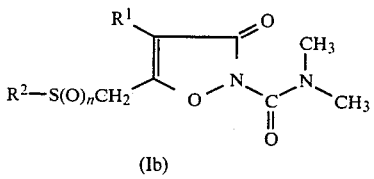

(Ib)

In the above reaction scheme, $R^1$ and $R^2$ are as defined above, X and Y represent halogen atoms, M represents an alkali metal and n represents 1 or 2.

Compounds of formula (Ia) may be prepared essentially by two different routes;

(1) reacting a compound of formula (II) with a mercaptide of formula $R^2SM$: or
(2) by reacting a compound of formula (III) with dimethylamine.

ROUTE 1

The mercaptide used in step 1(b) of this route may have been prepared in advance; alternatively, it may be prepared in situ, in a suitable reaction solvent prior to reaction with the compound of formula (II).

The reaction with the mercaptide is preferably effected in the presence of a solvent. The nature of the solvent employed is not critical, provided that it has no adverse effect upon the reaction. Suitable solvents include: alcohols, such as methanol or ethanol; ketones, such as acetone or methyl isobutyl ketone; ethers, such as tetrahydrofuran, dioxane or diglyme; water; dimethylformamide; dimethyl sulphoxide; hexamethylphosphoric triamide; or mixtures of any two or more thereof. Of these solvents, the alcohols are preferred.

The reaction conditions, for example, reaction temperature and proportions of reagents, are not critical to this reaction and will, accordingly, therefore normally be chosen having regard to the usual criteria applicable to this type of reaction.

The compound of formula (II) is itself novel and may be prepared from a compound of formula (VI) either by: step 1(a): heating a compound of formula (VI) with a dimethylcarbamic acid halide, in the absence of a base, and then separating the desired compound of formula (II) produced thereby from the simultaneously produced 3-dimethylcarbamoyloxy derivative by conventional means, such as chromatography or fractional crystallization; or step 1(a'): reacting the compound of formula (VI) with phosgene, in the absence of a base, to give a compound of formula (IV); and step 1(a'') reacting this compound of formula (IV) with a mixture of equimolar amounts of the calculated quantity of dimethylamine [calculated from the amount of the compound of formula (IV) produced] and a tertiary amine (such as triethylamine).

These reactions are preferably effected in the presence of a solvent, the nature of which is not critical, provided that it has no adverse effect upon the reaction. Suitable solvents include: aromatic hydrocarbons, such as benzene, toluene or xylene; chlorinated hydrocarbons, such as methylene chloride, chloroform or carbon tetrachloride; or mixtures of any two or more of these solvents.

ROUTE 2

In step 2(a) of this route, the compound of formula (VI) is reacted with a mercaptide of formula $R^2SM$ give a compound of formula (V), which is a novel compound. The reaction conditions and solvents, if employed, are the same as are used for step 1(b).

The resulting compound of formula (V) is then reacted with phosgene, in the absence of a base, to give a compound of formula (III). The excess phosgene is removed by evaporation and then, without any other purification, the resulting compound of formula (III) is reacted, in step 2(c), with a mixture comprising equimolar amounts of the calculated quantity of dimethylamine with a tertiary amine (such as triethylamine).

Steps 2(b) and 2(c) are preferably effected in the presence of a solvent, the nature of which is not critical, provided that it has no adverse effect upon the reaction; suitable solvents include those recommended for steps 1(a), 1(a') and 1(a'').

Compounds of formula (Ib), that is to say compounds of formula (I) in which A represents a sulphinyl or sulphonyl group, may be prepared by oxidizing the compound of formula (Ia) with a peroxide. Suitable peroxides include hydrogen peroxide, benzoyl peroxide and m-chloroperbenzoic acid, preferably m-chloroperbenzoic acid.

Where hydrogen peroxide is employed, it is preferably used in an approximately equimolar amount with respect to the compound of formula (Ia) and the rection is preferably effected at a temperature within the range from 5° to 25° C. This reaction is preferably effected in the presence of a solvent, the nature of which is not critical, provided that it has no adverse effect upon the reaction. Preferred solvents are aliphatic carboxylic acids, preferably acetic acid.

Where m-chloroperbenzoic acid is employed, we prefer that it should be used in an amount greater than equimolar with respect to the compound of formula (Ia). The reaction temperature is not particularly critical and the reaction will go to completion within a few hours at temperatures below ambient, even as low as 0° C. However, the reaction can also be effected at the reflux temperature of the solvent, if any, employed. The reaction is preferably effected in the presence of a solvent, the nature of which is not critical, provided that it has no adverse effect upon the reaction. The solvent is preferably organic and more preferably a halogenated hydrocarbon, such as methylene chloride, chloroform, carbon tetrachloride, chlorobenzene or o-dichlorobenzene.

The compounds of the present invention have a strong acaricidal activity for example against acarids of the genera Tetranychus or Panonychus and rust mites which are parasitic on fruit trees, vegetables and flowers. They are also active against various harmful insects of agricultural and horticultural importance, including aphids, the green rice leafhopper and the brown planthopper. They are also active against nematodes, such as root-knot nematodes.

The compounds of the invention may be employed to protect plants from attack by harmful insects or acarids or to treat plants already subject to such attack, by applying one or more of the compounds of the invention to the plants, to the general environment in which the plants are growing or to seeds prior to their growth to produce the plants.

The compounds may be employed in a wide variety of conventional forms, for example dusts, coarse dusts, microgranules, fine granules, wettable powders or emulsifiable concentrates. They are preferably employed in admixture with carriers or other auxiliary agents. The carrier employed may be natural or synthetic and organic or inorganic; it is mixed with the active ingredient to assist that ingredient to reach the material to be treated, and to make it easier to store, transport or handle the active ingredient.

Suitable solid carriers include: inorganic substances, such as clays (examples of which are kaolinite, montmorillonite and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; organic substances derived from vegetables, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes, such as carnauba wax and beeswax; or urea.

Examples of suitable liquid carriers include: paraffinic or naphthenic hydrocarbons, such as kerosine, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, chlorobenzene and o-chlorotoluene; ethers, such as dioxane and tetrahydrofuran; ketones, such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol monoethyl ether, ethylene glycol monophenyl ether, diethylene glycol monoethyl ether and diethylene glycol monobutyl ether; other polar organic solvents, such as dimethylformamide or dimethyl sulphoxide; and water.

Examples of gaseous carriers include air, nitrogen, carbon dioxide and the low boiling point fluorocarbons commonly used as propellants (such as those sold under the trade name "Freon"). The gaseous carriers may be used as simple mixtures with the active ingredients or may be used as propellants in aerosols.

In order to improve various of the properties of the active compounds, such as dispersion, emulsification, spreading, penetration or adhesion, the compounds of the invention may, if desired, be employed in admixture with various surface active agents, polymers or similar conventional additives, in order to improve wetting, deposition and absorption of the compositions and enhance the insecticidal and acaricidal effects.

Surface active agents may be employed in order to emulsify, disperse, wet, spread, bind, control disintegration of, improve fluidity of or rust-proof the composition or to stabilise the active ingredient. Any of the conventional classes of surface active agent, be they non-ionic, anionic, cationic or amphoteric, may be used. Normally, it is preferred to employ non-ionic and/or anionic surface active agents.

Examples of suitable non-ionic surface active agents include: the polymerization adducts of ethylene oxide with higher alcohols, such as lauryl alcohol, stearyl alcohol or oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di-alkylphosphoric acids, such as stearylphosphoric acid or dilaurylphosphoric acid, the polymerisation adducts of ethylene oxide with amines, such as dodecylamine or stearamide; the polymerization adducts of ethylene oxide with higher fatty acid esters of polyhydric alcohols, such as sorbitan, and the fatty acid esters themselves; and the polymerization adducts of ethylene oxide with propylene oxide. Examples of suitable anionic surface active agents include: alkyl sulphate salts, such as sodium lauryl sulphate or oleyl sulphate amine salt; alkyl sulphonate salts, such as sodium dioctyl sulphosuccinate or sodium 2-ethylhexene sulphonate; and aryl sulphonate salts, such as sodium isopropylnaphthalene sulphonate, sodium methylenebisnaphthalene sulphonate, sodium ligninsulphonate or sodium dodecylbenzene sulphonate.

Moreover, the compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the composition.

The above-mentioned carriers and various auxiliary agents may be used alone or in any desired combination, depending upon the type of preparation, the application and other factors.

Dusts may conveniently contain from 1 to 25% by weight of the active compounds, the remainder being a solid carrier.

Wettable powders may conveniently contain, for example, from 25 to 90% by weight of the active compound, the remainder being a solid carrier and a dispersing and wetting agent, if required, together with a protective colloidal agent, a thixotropic agent and an antifoaming agent.

Granules may conveniently contain from 1 to 35% by weight of the active compound, a major portion of the remainder being a solid carrier. The active compound is preferably homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the active compound and from 5 to 20% by weight of an emulsifying agent, the remainder being a liquid carrier, together with, if required, a corrosion inhibitor.

The compositions of the invention may be applied to crops bearing harmful insects and/or mites in a wide range of concentrations, for example from 100 to 1,000 ppm (as active ingredient). Most effective control of harmful insects and mites is achieved by applying the compositions to the leaves and stems of plants or to the soil.

The composition of the invention may additionally include one or more other insecticides, in order to broaden the insecticidal spectrum, and, in some cases, a synergistic effect may be observed.

Suitable insecticides include:

phosphorus-containing insecticides such as O,O-diethyl, O-(2-isopropyl-4-methyl-6-pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)-phosphorodithioate, O,O-dimethyl S-[2-(ethylthio)ethyl]phosphorodithioate, O,O-dimethyl 1-hydroxy-2,2,2-trichloroethylphosphonate, O,O-diethyl-O-(5-phenyl-3-isoxazolyl)phosphorothioate, O,O-dimethyl-O-(3-methyl-4-methylmercaptophenyl)thiophosphate, O-ethyl-O-p-cyanophenyl phenylphosphonothioate, O,O-dimethyl S-[1,2-bis(ethoxycarbonyl)ethyl]phosphorodithioate, 2-chloro-1-(2,4,5-trichlorophenyl)-vinyldimethyl phosphate, 2-chloro-1-(2,4-dichlorophenyl)vinyldimethyl phosphate, O,O-dimethyl O-p-cyanophenyl phosphorothioate, 2,2-dichlorovinyldimethylphosphate, ethyl mercaptophenylacetate O,O-dimethyl phosphorodithioate, S-[(6-chloro-2-oxo-3-benzooxazolinyl)methyl]-O,O-diethylphosphorodithioate, 4-methylthiophenyl dipropylphosphate, 2-chloro-1-(2,4-dichlorophenyl)vinyldiethylphosphate, O,O-diethyl-O-(3-oxo-2-phenyl-2H-pyridazin-6-yl)phosphorothioate, O,O-dimethyl S-(1-methyl-2-ethylsulphinyl)ethyl phosphorothioate, O,O-dimethyl S-phthalimidomethyl phosphorodithioate, dimethylmethylcarbamoylethylthioethyl thiophosphorothiolate, O,O-diethyl S-(N-ethoxycarbonyl-N-methylcarbamoylmethyl)phosphorodithioate, O,O-dimethyl-S-[2-methoxy-1,3,4-thiadiazol-5(4H)-onyl-(4)-methyl]dithiophosphate, 2-methoxy-4H-1,3,2-benzodioxaphosphorin 2-sulphide, O,O-diethyl-O-(3,5,6-trichloro-2-pyridyl)phosphorothioate, O,S-dimethyl-N-acetyl phosphoroamidothioate, O-2,4-dichlorophenyl O-ethyl S-propylphosphorodithioate, O,O-diethyl S-(2-chloro-1-phthalimidoethyl)phosphorodithioate and O-6-ethoxy-2-ethylpyrimidin-4-yl O,O-dimethylphosphorothioate;

carbamate-type insecticides such as 1-naphthyl N-methylcarbamate, S-methyl-N-[methylcarbamoyloxy]thioacetoimidate, 2-sec-butylphenyl-N-methylcarbamate, 2-isopropoxyphenyl-N-methylcarbamate, 1,3-bis(carbamoylthio)-2-(N,N-dimethylamino)propane hydrochloride and 2-dimethylamino-5,6-dimethylpyrimidin-4-yl dimethyl carbamate;

and other insecticides such as nicotine sulphate, milbemycin D, 6-methyl-2,3-quinoxalinedithiocyclic S,S-dithiocarbonate, 2,4-dinitro-6-sec-butylphenyldimethylacrylate, 1,1-bis(p-chlorophenyl)-2,2,2-trichloroethanol, azoxybenzene, di-(p-chlorophenyl)cyclopropyl carbinol, isopropyl-4,4-dichlorobenzylate, ethyl-4,4'-dichlorobenzylate, ethyl O-benzoyl-3-chloro-2,6-dimethoxybenzohydroxymate, isopropyl 4,4'-dibromobenzylate, tricyclohexyltin hydroxide, 2-(4-t-butylphenoxy)cyclohexylpropinylsulphide, 3-methyl-1,5-bis(2,4-xylyl)-1,3,5-triazapenta-1,4-diene, 2,4,5,4'-tetrachlorodiphenylsulphone, hexachlorohexahydromethanobenzodioxathiepine oxide, 5-dimethylamino-1,2,3-trithiane hydrogen oxalate and machine oil.

However, the nature of any such additional insecticide is not critical.

The composition of the invention may include one or more fungicides. Suitable fungicides are as follows.

Carbamate-type fungicides such as 3,3'-ethylenebis(tetrahydro-4,6-dimethyl-2H-1,3,5-thiadiazine-2-thione, zinc or manganese ethylenebisdithiocarbamate, bis(dimethyldithiocarbamoyl)disulphide, zinc propylenebisdithiocarbamate, methyl 1-(butylcarbamoyl)-2-benzimidazolcarbamate, 1,2-bis(3-methoxycarbonyl-2-thioureido)benzene and bisdimethyldithiocarbamoyl zinc ethylenebisdithiocarbamate;

dicarboximide-type fungicides such as N-trichloromethylthio-4-cyclohexene-1,2-dicarboximide and N-tetrachloroethylthio-4-cyclohexene-1,2-dicarboximide;

oxazine-type fungicides such as 5,6-dihydro-2-methyl-1,4-oxazine-3-carboxanilide-4,4-dioxide;

naphthoquinone-type fungicides such as 2,3-dichloro-1,4-naphthoquinone;

and other fungicides such as 3-hydroxy-5-methylisoxazole, 5-ethoxy-3-trichloromethyl-1,2,4-thiadiazole, 2,4-dichloro-6-(o-chloroanilino)-1,3,5-triazine, 2,3-dicyano-1,4-dithioanthraquinone, copper 8-quinolate, polyoxin, validamycin, tetrachloroisophthalonitrile, 2-(1-methylpropyl)-4,6-dinitrophenol $\beta,\beta$-dimethylacrylate, triphenyltin hydroxide, phytomycin, dinitromethylheptylphenyl crotonate, 5-butyl-2-dimethylamino-6-methylpyrimidin-4-ol, 6-(3,5-dichloro-4-methylphenyl)-3-(2H)pyridazinone, 6-(3-bromophenyl)-3-(2H)pyridazinone, N-(2,6-dimethylphenyl)-N-methoxyacetylalanine methyl ester and bis(8-guadinooctyl)amine acetate.

The invention is further illustrated by the following Examples and the preparation of certain of the starting materials used in these is described in the following Preparations.

EXAMPLE 1

2-Dimethylcarbamoyl-5-methylthiomethyl-4-isoxaxolin-3-one 2.5 g of a 15% aqueous solution of sodium methanethiolate were diluted with 10 ml of ethanol, and then 1023 mg of crystalline 5-chloromethyl-2-dimethylcarbamoyl-4-isoxazolin-3-one were added, with stirring at room temperature, to the resulting solution. The mixture was stirred at room temperature for a further 30 minutes, after which the ethanol and water were distilled off.

The residue was subjected to chromatography through silica gel, eluted with a 10:1 by volume mixture of benzene and acetone. The eluate was concentrated by evaporation under reduced pressure and the residue was recrystallized from diisopropyl ether, to give 788 mg (yield 72.9%) of 2-dimethylcarbamoyl-5-methylthiomethyl-4-isoxazolin-3-one, in the form of colourless prisms melting at 91°–92° C.

EXAMPLE 2

4-Chloro-2-dimethylcarbamoyl-5-ethylthiomethyl-4-isoxazolin-3-one

A solution of 0.5 ml of phosgene in 5 ml of benzene was added to 581 mg of 4-chloro-3-hydroxy-5-ethylthiomethylisoxazole, and then the mixture was stirred at room temperature for 5 hours, after which the solvent and excess phosgene were distilled off, to produce 4-chloro-2-chlorocarbonyl-5-ethylthiomethyl-4-isoxazolin-3-one. This was dissolved, without purification, in 30 ml of benzene and an equimolar mixture of the calculated amount of dimethylamine with triethylamine in 5 ml of benzene was added, with stirring, at room temperature. The mixture was stirred for a further 30 minutes and then washed, in turn, with 0.1N sulphuric acid (twice, 10 ml each time) and then water (3 times, 10 ml each time). The benzene layer was dried over anhydrous sodium sulphate, and the solvent was distilled off. The residue was purified by column chromatography through silica gel, eluted with a 25:1 by volume mixture of benzene and acetone. The solvent was distilled from the eluate, to give 661 mg (yield 83.2%) of the title compound in the form of an oil having a refractive index, $n_D^{22} = 1.5454$.

EXAMPLE 3

4-Chloro-2-dimethylcarbamoyl-5-methylsulphinylmethyl-4-isoxaolin-3-one 530 mg of 4-chloro-2-dimethylcarbamoyl-5-methylthiomethyl-4-isoxazolin-3-one were dissolved in 10 ml of methylene chloride, and then to this solution was added dropwise over 35 minutes, with ice-cooling and stirring, a solution of 430 mg of m-chloroperbenzoic acid in 5 ml of methylene chloride. The mixture was then stirred at room temperature for a further 4.5 hours, after which it was washed, in turn, with 10 ml of a 5% w/v aqueous solution of sodium hydrogen carbonate and then twice, each time with 10 ml of water.

The organic phase was dried over anhydrous sodium sulphate, and the solvent was distilled off. The residue was subjected to column chromatography through silica gel, eluted with 30:1 by volume mixture of benzene and ethanol. The solvent was distilled from the eluate, to give 363 mg (yield 64.8%) of the title compound, in the form of crystals melting at 101°–102° C.

These crystals were further recrystallized from a mixture of methylene chloride and diisopropyl ether, to give the title compound in pure form, melting at 103°–104° C.

EXAMPLE 4

2-Dimethylcarbamoyl-5-ethylsulphonylmethyl-4-isoxazolin-3-one

A solution of 740 mg of 3-dimethylcarbamoyl-5-ethylthiomethyl-4-isoxazolin-3-one in 5 ml of methylene chloride was added dropwise over 30 minutes, with stirring, to an ice-cooled solution of 1.3 g of m-chloroperbenzoic acid in 25 ml of methylene chloride. The mixture was stirred for a further 30 minutes, after which crystals of m-chlorobenzoic acid were filtered off. The solvent was distilled from the filtrate, and the residue was recrystallized from diethyl ether, to give 730 mg (yield 87.0%) of the title compound, in the form of colourless crystals melting at 100°–101° C.

EXAMPLE 5

4-Chloro-2-dimethylcarbamoyl-5-methylsulphonylmethyl-4-isoxazolin-3-one 363 mg of 4-chloro-2-dimethylcarbamoyl-5-methylsulphinylmethyl-4-isoxazolin-3-one were dissolved in 20 ml of methylene chloride, and then 300 mg of crystals of m-chloroperbenzoic acid were added little by little, whilst ice-cooling and stirring. The mixture was allowed to stand overnight at room temperature, and was then washed, in turn, with 20 ml of a 5% w/v aqueous solution of sodium hydrogen carbonate and then twice, each time with 20 ml of water. The washings were combined and then extracted twice, each time with 10 ml of chloroform. The organic phases were combined and dried over anhydrous sodium sulphate, after which the solvent was distilled off. The residue was recrystallized from a mixture of methylene chloride and diisopropyl ether, to give 337 mg (yield 87.5% of theory) of the title compound in the form of crystals melting at 129°–129.5° C.

PREPARATION 1

5-Chloromethyl-2-dimethylcarbamoyl-4-isoxazolin-3-one

A mixture of 1.35 g of 5-chloromethyl-3-hydroxyisoxazole, 50 ml of hexane and 1.5 g of dimethylcarbamoyl chloride was refluxed for 6 hours. The solvent was then distilled from the reaction mixture and the residue was subjected to column chromatography through silica gel.

258 mg (yield 19.1%) of the original 5-chloromethyl-3-hydroxyisoxazole were recovered first, eluted with diisopropyl ether. 737 mg (yield 36.9%) of 5-chloromethyl-3-dimethylcarbamoyloxyisoxazole were obtained next, followed by 890 mg (yield 43.4%) of the title compound (melting at 89°–90° C. after recrystallization from diisopropyl ether) on elution with a 10:1 by volume mixture of benzene and acetone.

Following the same procedure, the following compounds were also prepared:
5-bromomethyl-4-chloro-2-dimethylcarbamoyl-4-isoxazolin-3-one, melting at 105°–107° C.;
4-bromo-5-bromomethyl-2-dimethylcarbamoyl-4-isoxazolin-3-one, melting at 71°–72° C.

PREPARATION 2

2-Chlorocarbonyl-5-chloromethyl-4-isoxazolin-3-one

A mixture of 673 mg of 5-chloromethyl-3-hydroxyisoxazole, 19 ml of benzene and about 1 ml of liquified phosgene was stirred at room temperature for 5 hours. At the end of this time, the excess phosgene and the solvent were distilled off, giving 900 mg (yield 100% of theory) of the title compound, in the form of a colourless oil having a refractive index, $n_D^{24} = 1.5391$.

Following the same procedure, the following compounds were also prepared:
3-chloro-2-chlorocarbonyl-5-chloromethyl-4-isoxazolin-3-one, $n_D^{24} = 1.5507$;
4-bromo-2-chlorocarbonyl-5-chloromethyl-4-isoxazolin-3-one, $n_D^{24} = 1.5714$;
2-chlorocarbonyl-5-chloromethyl-4-iodo-4-isoxazolin-3-one, $n_D^{24} = 1.5989$;
5-bromomethyl-4-chloro-2-chlorocarbonyl-4-isoxazolin-3-one, $n_D^{\approx} = 1.5782$;

4-bromo-5-bromomethyl-2-chlorocarbonyl-4-isoxazolin-3-one one, $n_D^{25}=1.5963$.

PREPARATION 3

4-Chloro-5-chloromethyl-2-dimethylcarbamoyl-4-isoxazolin-3-one 254 mg of 4-chloro-2-chlorocarbonyl-5-chloromethyl-4-isoxazolin-3-one were dissolved in 5 ml of benzene, and then a solution of 48 mg of dimethylamine and 107 mg of triethylamine in 2 ml of benzene were added, with stirring, at room temperature. The mixture was stirred for a further 10 minutes, after which it was washed, in turn, with 2 ml of 0.1N sulphuric acid and water (twice, 5 ml each time). The organic phase was dried over anhydrous sodium sulphate and the solvent was distilled off. The residue was purified by column chromatography through silica gel eluted with a 20:1 by volume mixture of benzene and acetone. The solvent was distilled from the eluate and the residue was recrystallized from diisopropyl ether, to give 159 mg (yield 62.8%) of the title compound in the form of crystals, melting at 107°–108° C.

Following the procedure described in Preparation 3, the following compounds were also prepared:

4-bromo-5-chloromethyl-2-dimethylcarbamoyl-4-isoxazolin-3-one, melting at 121°–122° C.; and 5-chloromethyl-2-dimethylcarbamoyl-4-iodo-4-isoxazolin-3-one, melting at 148°–149° C.

The agricultural compositions of the invention are illustrated by the following Formulations, in which all parts are by weight.

Formulation 1

Dust 5 parts of Compound No. 3, 50 parts of talc and 45 parts of kaolin were thoroughly blended to give a dust.

Formulation 2

Wettable powder 50 parts of Compound No. 4, 29 parts of clay, 10 parts of diatomaceous earth, 5 parts of white carbon, 3 parts of sodium ligninsulphonate, 2 parts of Newcol 1106 (trademark, Nippon Nyukazai) and 1 part of polyvinyl alcohol were thoroughly blended in a mixer and then pulverized three times with a hammer mill to give a wettable powder.

Formulation 3

Granules 70 parts of Compound No. 26 were finely pulverized, mixed with 30 parts of clay and then blended in a mixer to make a premix. 10 parts of the premix, 60 parts of clay and 30 parts of bentonite were thoroughly blended in a mixer and then a suitable amount of water was added to the mixture. The mixture was then compounded in a kneader, extruded through a screen whose apertures were of diameter 0.8 mm and then dried at 50° C. in a forced air oven. The dried compound was granulated with a sifter to give granules.

Formulation 4

Emulsifiable concentrate 20 parts of Compound No. 9, 10 parts of Sorpol SM-200 (trade name, Toho Chemical) and 70 parts of xylene were uniformly blended to give an emulsifiable concentrate.

The activites of the compositions of the invention are shown by the following Experiments.

EXPERIMENT 1

Control of the two-spotted spider mite

Test suspensions containing 300 ppm of each of the active compounds shown in Table 1 and 0.01% w/v of a spreader (Gramin, trade name) were prepared. Leaves of cowpea, bearing adult two-spotted spider mites (Tetranychus urticae), were dipped for 10 seconds into each suspension. After air-drying, the leaves were allowed to stand in a room maintained at 25° C. A mortality of 100% after 72 hours was taken as 4, a 99–80% mortality was taken as 3 and a 79–20% mortality was taken as 2. Each test group contained on average 50 adult mites. The results are shown in Table 1.

TABLE 1

| Compound No. | Acaricidal effect | Compound No. | Acaricidal effect |
|---|---|---|---|
| 1 | 4 | 21 | 4 |
| 2 | 4 | 22 | 4 |
| 4 | 4 | 23 | 4 |
| 10 | 4 | 24 | 4 |
| 11 | 4 | 25 | 4 |
| 12 | 4 | 26 | 4 |
| 14 | 4 | 28 | 4 |
| 19 | 4 | Control | 2 |
| 20 | 4 | Compound (A) | |

Compound (A): 2-dimethylcarbamoyl-5-methyl-4-isoxazolin-3-one.

EXPERIMENT 2

Control of the green peach aphid (a) Contact activity

A wettable powder was prepared by homogeneously mixing and pulverizing three times in a hammer mill 10 parts of one of the test compounds, 4 parts of sodium dodecylbenzene sulphonate, 2 parts of polyvinyl alcohol and 84 parts of clay. The wettable powder thus prepared was then diluted with water to the pre-determined concentration and then 0.01% w/v of Gramin (a spreader) was added.

The resulting diluted solution was then sprayed onto the leaves of a Chinese mustard "Komatsuna" bearing green peach aphids (Myzus persicae) in an amount of 10 ml per leaf. The leaf stalk of each leaf was then placed in a 30 ml bottle containing water and the mouth of the bottle was plugged with cotton wool. After 72 hours at 25° C. the percentage mortality of the aphids was assessed and the results are shown in Table 2.

(b) Systemic activity

Test suspensions were prepared as described above and then diluted to pre-determined concentrations. The suspensions were then poured into 30 ml bottles. Leaves of the Chinese mustard "Komatsuna" bearing green peach asphids were then placed in the bottles and the mouths of the bottles were plugged with cotton wool. The bottles were maintained at 25° C. for 72 hours, and then the percentage mortality of the aphids were assessed. The results are shown in Table 2.

TABLE 2

| Compound No. | Contact activity ppm | | | Systemic activity ppm | |
|---|---|---|---|---|---|
| | 6.25 | 3.13 | 1.56 | 0.8 | 0.4 |
| 1 | 100 | 100 | 84 | 100 | 100 |
| 2 | 100 | 100 | 84 | 100 | 100 |
| 8 | 100 | 100 | 65 | 100 | 94 |

TABLE 2-continued

| Compound No. | Contact activity ppm | | | Systemic activity ppm | |
|---|---|---|---|---|---|
| | 6.25 | 3.13 | 1.56 | 0.8 | 0.4 |
| 9 | 100 | 91 | 53 | 100 | 92 |
| 11 | 84 | 67 | 47 | 100 | 54 |
| 13 | 100 | 88 | 55 | 82 | 69 |
| 14 | 83 | — | — | 100 | 82 |
| 19 | 100 | 78 | — | 100 | 78 |
| 20 | 67 | — | — | 100 | 85 |
| 21 | 100 | 78 | 35 | 100 | 100 |
| 22 | 100 | 42 | — | 85 | 50 |
| Control Compound (A) | 42 | 35 | 5 | 61 | 41 |

EXPERIMENT 3

Control of the green rice leafhopper and the brown planthopper

Dusts containing 2% by weight of each of the active compounds shown in Table 3 were sprayed in plastic cylinders onto pots in which rice seedlings had been transplanted.

10–15 of the final instar larvae of the green rice leaf hopper (*Naphotettix cincticeps*) or of the brown planthopper. (*Nilaparvata lugens*) known to be resistant were released in each cylinder. The pots were maintained at 25° C. for 72 hours, and then the percentage mortality of the larvae was assessed from the average of two pots per test.

The results are shown in Table 3.

TABLE 3

| Compound No. | Green rice leafhopper | | Brown planthopper | |
|---|---|---|---|---|
| | 1.41* | 0.71* | 1.41* | 0.71* |
| 1 | 100 (%) | 100 (%) | 100 (%) | 100 (%) |
| 2 | 100 | 50 | 100 | 58 |
| 8 | 100 | 90 | 100 | 96 |
| 19 | 100 | 68 | 100 | 82 |
| Control Compound (A) | 46 | 7 | 41 | 13 |

*Amount (kg) of 2% dust per 10 are (converted value)

EXPERIMENT 4

Control of the southern root-knot nematode

Wettable powders containing each of the active compounds of the invention shown in Table 4 were diluted with water to a concentration of 100 ppm.

About 300 per test of the second instar larvae of the southern root-knot nematode (*Meloidogyne incognita*), within 24 hours after incubation, were immersed in the test suspension for 24 hours, maintained at 25° C.

After the treatment, the nematodes were kept in a Baermann's funnel at room temperature for 72 hours. At the end of this period, the number of living nematodes which passed the funnel was counted with a microscope. The results are shown in Table 4 in terms of the percentage mortality.

TABLE 4

| Compound No. | Southern root-knot nematode % mortality |
|---|---|
| 1 | 100 |
| 2 | 100 |
| 8 | 100 |
| 9 | 100 |
| 18 | 70 |
| 19 | 98 |
| 21 | 95 |
| 22 | 90 |
| 23 | 95 |
| 24 | 50 |
| 25 | 97 |
| 26 | 92 |
| 27 | 96 |
| 28 | 95 |

We claim:

1. A compound of the formula (I):

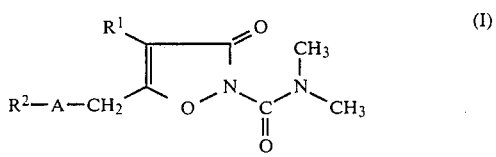

wherein:
$R^1$ represents a hydrogen atom or a halogen atom;
$R^2$ represents an alkyl group, a $C_2$–$C_6$ alkenyl group, a $C_2$–$C_6$ alkynyl group, an aralkyl group, a substituted aralkyl group, an aryl group or a substituted aryl group; and
A represents a sulphur atom, a sulphinyl group or a sulphonyl group.

2. The compound as claimed in claim 1, wherein:
$R^1$ represents a hydrogen atom or halogen atom; and
$R^2$ represents a $C_1$–$C_8$ alkyl group, a $C_2$–$C_6$ alkenyl group, a $C_2$–$C_6$ alkynyl group or a benzyl, phenethyl, phenyl or naphthyl group which is unsubstituted or has at least one halogen, $C_1$–$C_6$ alkyl or $C_1$–$C_6$ alkoxy substituent on its aromatic ring.

3. The compound as claimed in claim 1, wherein:
$R^1$ represents a hydrogen atom, a chlorine atom or a bromine atom; and
$R^2$ represents a straight chain $C_1$–$C_4$ alkyl group or a $C_3$–$C_4$ alkenyl group.

4. An insecticidal and acaricidal composition comprising a carrier or diluent in admixture with an active agent wherein the active agent is at least one compound of the formula (I):

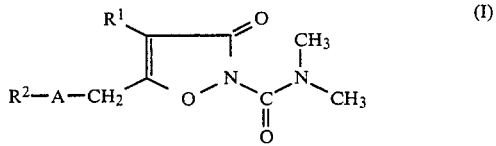

wherein:
$R^1$ represents a hydrogen atom or a halogen atom;
$R^2$ represents an alkyl group, a $C_2$–$C_6$ alkenyl group, a $C_2$–$C_6$ alkynyl group, an aralkyl group, a substituted aralkyl group, an aryl group or a substituted aryl group; and
A represents a sulphur atom, a sulphinyl group or a sulphonyl group.

5. The composition as claimed in claim 4, wherein:
$R^1$ represents a hydrogen atom or halogen atom; and
$R^2$ represents a $C_1$–$C_8$ alkyl group, a $C_2$–$C_6$ alkenyl group, a $C_2$–$C_6$ alkynyl group or a benzyl, phenethyl, phenyl or naphthyl group which is unsubstituted or has at least one halogen, $C_1$–$C_6$ alkyl or $C_1$–$C_6$ alkoxy substituent on its aromatic ring.

6. The composition as claimed in claim 4, wherein:
$R^1$ represents a hydrogen atom, a chlorine atom or a bromine atom; and
$R^2$ represents a straight chain $C_1$–$C_4$ alkyl group or a $C_3$–$C_4$ alkenyl group.

7. The composition as claimed in claim 4, wherein said active agent is 2-dimethylcarbamoyl-5-methylthiomethyl-4-isoxazolin-3-one.

8. The composition as claimed in claim 4, wherein said active agent is 2-dimethylcarbamoyl-5-ethylthiomethyl-4-isoxazolin-3-one.

9. The composition as claimed in claim 4, wherein said active agent is 4-chloro-2-dimethylcarbamoyl-5-methylthiomethyl-4-isoxazolin-3-one.

10. The composition as claimed in claim 4, wherein said active agent is 4-chloro-2-dimethylcarbamoyl-5-ethylthiomethyl-4-isoxazolin-3-one.

11. The composition as claimed in claim 4, wherein said active agent is 2-dimethylcarbamoyl-5-methylsulphinylmethyl-4-isoxazolin-3-one.

12. 2-Dimethylcarbamoyl-5-methylthiomethyl-4-isoxazolin-3-one of the formula of claim 1.

13. 2-Dimethylcarbamoyl-5-ethylthiomethyl-4-isoxazolin-3-one of the formula of claim 1.

14. 4-Chloro-2-dimethylcarbamoyl-5-methylthiomethyl-4-isoxazolin-3-one of the formula of claim 1.

15. 4-Chloro-2-dimethylcarbamoyl-5-ethylthiomethyl-4-isoxazolin-3-one of the formula of claim 1.

16. 2-Dimethylcarbamoyl-5-methylsulphinylmethyl-4-isoxazolin-3-one of the formula of claim 1.

* * * * *